United States Patent [19]

Meybeck et al.

[11] Patent Number: 5,164,182
[45] Date of Patent: Nov. 17, 1992

[54] COMPOSITION CONTAINING A MULBERRY EXTRACT INCORPORATED INTO HYDRATED LIPIDIC LAMELLAR PHASES OF LIPOSOMES

[75] Inventors: Alain Meybeck, Courbevoie; Marc Dumas, Colombes, both of France

[73] Assignee: LVMH Recherche, Colombes Cedex, France

[21] Appl. No.: 458,744

[22] PCT Filed: Jun. 10, 1988

[86] PCT No.: PCT/FR88/00296

§ 371 Date: Dec. 11, 1989

§ 102(e) Date: Dec. 11, 1989

[87] PCT Pub. No.: WO88/09654

PCT Pub. Date: Dec. 15, 1988

[30] Foreign Application Priority Data

Jun. 12, 1987 [FR] France ............................. 87 08235

[51] Int. Cl.⁵ ..................... A61K 35/78; A61K 72/22; A61K 31/685
[52] U.S. Cl. ................. 424/195.1; 424/450; 514/78; 514/844

[58] Field of Search ............... 424/195.1, 450; 514/78, 514/844, 886

[56] References Cited

U.S. PATENT DOCUMENTS 3,856,934 12/1974 Kligman ................................ 424/62

FOREIGN PATENT DOCUMENTS 88046 9/1983 European Pat. Off. ............ 424/450
152414 8/1985 Japan .................................. 424/450

*Primary Examiner*—John W. Rollins
*Attorney, Agent, or Firm*—Bryan Cave

[57] ABSTRACT

A composition comprising hydrated lipidic lamellar phases of liposomes containing a mulberry component. The composition may also contain kojic acid or its salts or esters, hydroquinone, or a mixture of kojic acid or its salts or esters and hydroquinone. This composition has skin-lightening properties or anti-inflammatory activity and has pharmaceutical and cosmetic applications. A method for lightening the skin or for applying anti-inflammatory formulation to the skin by applying to the skin a composition comprising hydrated lipidic lamellar phases or liposomes containing a mulberry component.

66 Claims, No Drawings

COMPOSITION CONTAINING A MULBERRY EXTRACT INCORPORATED INTO HYDRATED LIPIDIC LAMELLAR PHASES OF LIPOSOMES

The present invention relates essentially to a composition based on hydrated lipidic lamellar phases or on liposomes containing an extract of mulberry, preferably Morus Alba, and to a pharmaceutical composition, especially a dermatological composition, with skin-lightening or antiinflammatory activity, or a cosmetic composition in which it is incorporated. The extract preferred according to the invention is obtained from the aerial or underground parts of the mulberry, preferably Morus Alba L. or Morus Rubra, especially the leaves, the ends of the stems and the bark of the shoots or roots.

It is known that the mulberry grows naturally everywhere in the mountains and fields. It is a plant which has long been cultivated for sericulture. Parts of the mulberry, in particular the bark of its roots or shoots, or extracts of this bark, also called "sohakuhi", have already been in use for a very long time, especially in Chinese medicine.

Therapeutic virtues, especially antiphlogistic, diuretic and febrifugal properties, are attributed to the dried bark of mulberry shoots or roots, or to extracts thereof, as a remedy for pain, in the treatment of bronchitis, asthma etc.

The presence of bleaching compounds has relatively recently been discovered in the extract of the bark of mulberry shoots or roots, or sohakuhi, these compounds having been incorporated into cosmetic compositions in order to inhibit the activity of tyrosinase—which is an enzyme responsible for the coloration of the skin—thereby producing a skin-lightening effect (see C.A. Essential Oils, Cosmetics, volume 88, 1978, page 227, abstract 88:65874z, or Japanese patent document A-50-135-236).

For pharmacological studies, see the document Japan Journal of Pharmacology, 1976, 26 (4), 461–9, or C.A., volume 85, 1976, page 48, abstract 85:137465e. An application of mulberry extract as an antidiabetic is described in French patent document A-2 336 941.

Furthermore, numerous substances have already been isolated from the extract of the bark of mulberry shoots or roots, the vast majority of which are active principles. They are generally flavones, flavone derivatives and, in particular, kuwanones.

The first document relates to the isolation of a white crystalline powder (C.A , 45 (1951), abstract 9513g).

The isolation of a yellowish white powder is described in C.A., 57 (1962), abstract 3970g.

The isolation of 4 flavones was first described in Tetrahedron Letters no. 14, pages 1715–1719, 1968, with a corresponding abstract in Chemical Abstracts, volume 69, 1968, page 3340, abstract 35869s. Other flavones, such as rubraflavone A, B, C or D, are described in Indian Journal of Chemistry, volume 12, May 2, 1974, pages 431–436, with an abstract in C.A., volume 82, 1975, page 557, abstract 57520s. -Tocopherol has also been isolated from the bark of mulberry roots (C.A., volume 82, 1975, page 213, abstract 70272a). Other flavones, such as mulberranol, and a phenol, such as alboctalol, have also been isolated (C.A., 86 (1977), page 551, abstract 86:139896r). Subsequently, other flavones, such as morusine and cyclomorusine, have been isolated and described in C.A., volume 87, 1977, page 566, abstract 87:167917n.

The isolation of kuwanone E is also described in C.A , volume 89, 1978. abstract 89:211925f.

The isolation of kuwanone A, B and C and oxydihydromorusine is also described in C.A., volume 89, 1978, page 429, abstract 89:103271c.

The synthesis of tetrahydrokuwanone C tetramethyl ether has also been described in Heterocycles, volume 9, no. 10, 1978, pages 1355–1366.

A more detailed description of the isolation of kuwanone E is also described in Heterocycles, volume 9, no. 9, 1978.

The isolation of phenolic constituents is described in C.A., volume 90, 1979, abstract 90:83661y. The structure of moracenine D, constituting a particular flavone, is described as having a hypotensive activity in Heterocycles, volume 16, no. 6, 1981, and also in C.A., volume 94, 1981, abstract 94:117759m, where its extraction process is also described.

The isolation of mulberrofuran B is also described in C.A., volume 95, 1981, abstract 95:147106j.

Thus it can be seen that the use of the extract of the bark of mulberry root as a pharmaceutical or cosmetic product is well known, as is the isolation of a number of active substances.

For a detailed summary of the extraction processes, reference may also be made to Heterocycles, volume 15, no. 2, 1981, pages 1531 to 1567.

Furthermore, the document C.A., volume 93, 1980, abstract 93:368620, describes the encapsulation of quercetin in liposomes for producing effects on the synthesis of DNA and the production of lactate and for increasing the level of adenosine 3',5'-cyclic monophosphate.

Extracts of leaves of mulberry (Morus Alba) have also been used for the preparation of cosmetic compositions on account of their eudermic and eutrophic properties (see French patent document A-2 582 941).

A product with a substantial skin-lightening activity which may be mentioned is the association of active principles known as the "Kligman trio", which is based on a combination of vitamin A acid or tretinoin, hydroquinone and a corticoid (dexamethasone). However, the use of such a product has been limited in practice because of a considerable irritant character caused by the presence of vitamin A acid, which is well known for its irritant character, and undesirable effects due to hypervitaminosis A (see "The Journal of Investigative Dermatology", volume 73, no. 5, part I, pages 354–358, and in particular the penultimate paragraph on page 357, published in 1979).

This explains the interest in mulberry extracts, especially extracts of the bark of mulberry shoots or roots, which do not have the above-mentioned disadvantages although their skin-lightening activity is low.

Furthermore, the use of hydrated lipidic lamellar phases or of liposomes is already known in pharmaceutical compositions or cosmetic compositions in which a variety of active principles are incorporated (French patent document A-2 540 381).

It has now been discovered, totally surprisingly and unexpectedly, that the incorporation of the above-mentioned extract of mulberry, especially of mulberry shoots or roots, or of any active substance which may have been isolated from such a mulberry extract, like a flavone, in particular a kuwanone, has an enhanced activity when at least part of this extract or this substance is incorporated into a hydrated lipidic lamellar phase or into liposomes. This pertains to all the activities known for mulberry extracts or substances isolated from such extracts, in particular kuwanones. An even more radical improvement in the activity has been observed in the case of the skin-lightening activity and the antiinflammatory activity.

It is possible to deduce from this that the incorporation of mulberry extracts into hydrated lipidic lamellar phases or into liposomes has some kind of synergistic effect.

Such a synergistic effect is also obtained if a combination of mulberry extracts, or an active substance isolated from such extracts, with kojic acid or derivatives thereof, especially salts or esters thereof, is incorporated into the hydrated lipidic lamellar phases or into the liposomes.

An appreciable improvement in the activity is also observed if the mulberry extracts are combined with hydroquinone by itself or a mixture of hydroquinone with kojic acid or derivatives thereof, especially salts or esters thereof.

Thus the object of the present invention is to solve the novel technical problem which consists in providing a novel formulation of mulberry extract, or of any active substance isolated from such an extract or reconstituted by chemical synthesis, making it possible to potentiate their efficacy so as to enable them to be used in pharmaceutical compositions, especially dermatological compositions, with skin-lightening or anti-inflammatory activity, or as cosmetic compositions.

The present invention provides the first satisfactory solution to this novel technical problem.

Thus, according to a first aspect, the present invention provides a composition based on hydrated lipidic lamellar phases or on liposomes, wherein the said hydrated lipidic lamellar phases or the said liposomes contain at least part of an extract of mulberry, especially Morus Alba L. or Morus Rubra, or at least one active substance isolated from such an extract or obtained by chemical synthesis, in particular a kuwanone.

According to a particular characteristic of this composition, it contains an extract of leaves, ends of stems, bark of shoots or bark of roots of mulberry, obtained by extraction with a solvent which is preferably selected from the group consisting of a polar solvent, in particular an alcoholic, aqueous-alcoholic or ether solution, an apolar organic solvent such as n-hexane or benzene, or a combination of both, advantageously by first carrying out an extraction with an apolar organic solvent and then carrying out an extraction with a polar solvent.

In one advantageous embodiment of the invention, the above-mentioned hydrated lipidic lamellar phases of the above-mentioned composition also contain, at least in part, kojic acid or derivatives thereof, especially salts or esters thereof.

In another particularly advantageous embodiment of the invention, the above-mentioned hydrated lipidic lamellar phases contain, at least in part, hydroquinone by itself or mixed with kojic acid or derivatives thereof, especially salts or esters thereof.

In one modified embodiment of this composition, the above-mentioned extract of the said composition, by itself or mixed with hydroquinone and/or kojic acid or derivatives thereof, especially salts or esters thereof, is introduced into the lipidic phase of the hydrated lipidic lamellar phases or of the liposomes.

In another modified embodiment of this composition, the above-mentioned extract of the said composition, by itself or mixed with hydroquinone and/or kojic acid or derivatives thereof, especially salts or esters thereof, is introduced into the aqueous phase of the hydrated lipidic lamellar phases or of the liposomes.

According to a second aspect, the present invention further relates to a pharmaceutical composition, especially a dermatological composition, with skin-lightening or antiinflammatory activity, or a cosmetic composition, which comprises a composition based on hydrated lipidic lamellar phases or on liposomes, such as defined above.

Preferably, the proportion by weight of dry extract of mulberry or any active substance obtained from such an extract or by chemical synthesis is between 0.005 and 1%, relative to the total weight of the composition; it is more preferably between 0.005 and 0.1% and most preferably between 0.05 and 0.1%, relative to the total weight of the composition.

Such a composition can also contain, at least in part, in the hydrated lipidic lamellar phases, kojic acid or derivatives thereof, especially salts or esters thereof, preferably in a proportion of between 0.5 and 4% by weight, relative to the total weight of the composition, more preferably of between 0.5 and 2% and most preferably of about 1%.

Moreover, if the composition contains hydroquinone, at least part of the latter is incorporated into the hydrated lipidic lamellar phases in a proportion preferably of between 0.5 and 6% by weight, relative to the total weight of the composition, more preferably of between 0.5 and 4% and most preferably of about 2%.

Likewise, in a first modified embodiment of this pharmaceutical composition, especially dermatological composition, or cosmetic composition, the above-mentioned extract, by itself or mixed with hydroquinone and/or kojic acid or derivatives thereof, especially salts or esters thereof, can be introduced into the lipidic phase of the hydrated lipidic lamellar phases or of the liposomes, whereas in another modified embodiment, the above-mentioned extract, by itself or mixed with hydroquinone and/or kojic acid or derivatives thereof, especially salts or esters thereof, can be introduced into the aqueous phase of the hydrated lipidic lamellar phases or of the liposomes.

The invention also covers the above-mentioned processes for the preparation of the composition based on hydrated lipidic lamellar phases or on liposomes, or the pharmaceutical composition, especially dermatological composition, with skin-lightening or anti-inflammatory activity, or cosmetic composition, wherein at least part of an extract of mulberry, especially Morus Alba L. or Morus Rubra, or at least one active substance isolated from such an extract or obtained by chemical synthesis, in particular a kuwanone, is incorporated into the said hydrated lipidic lamellar phases or the said liposomes.

In the present description and the claims, the term "lipidic" in the expression "lipidic lamellar phase" covers all substances comprising a so-called fatty carbon chain, generally of more than 5 carbon atoms.

According to the invention, amphiphilic lipids are used, i.e. lipids consisting of molecules possessing a hydrophilic group, which can equally well be ionic or non-ionic, and a lipophilic group, these amphiphilic lipids being capable of forming lipidic lamellar phases in the presence of an aqueous phase. The following may be mentioned in particular among these lipids: phospholipids, phosphoaminolipids, glycolipids, polyethoxylated fatty alcohols and optionally polyethoxylated polyol esters. Such substances consist for example of an egg or soya lecithin, a phosphatidylserine, a sphingomyelin, a cerebroside or an ethoxylated polyglycerol stearate.

Further objects, characteristics and advantages of the invention will become clear on reading the following explanatory description given with reference to several illustrative Examples, which cannot therefore in any way limit the scope of the invention. In the Examples, the percentages are given by weight, unless indicated otherwise.

EXAMPLE 1 OF THE INVENTION

A - Preparation of a composition in powder form containing a dry extract of the bark of mulberry root The extract of the bark of mulberry root used is an extract marketed by the Japanese company Marusen Seiyaku Co. Limited, consisting in this case of lot no. 412033, which is in the form of a transparent liquid with a weak characteristic odor, a slightly yellowish brown color, a pH of 4.4, a density of 0.951, a proportion of residue after evaporation of 1.83% by weight/volume, a UV absorption E 1%, 1 cm of 0.61 at 280 nm, a maximum heavy metal content of 10 ppm and a maximum arsenic content of 2 ppm, with a positive response to the terpenoid identification test.

40 ml of this mulberry extract are taken and evaporated to dryness. This dry extract is then dissolved in 300 ml of methylene chloride to which 20 g of hydrogenated soya lecithin are added, if appropriate in the presence of a lipophilic antioxidant, for example 0.6 g of α-tocopherol.

The solution obtained is atomized at 65° C. in the manner described in U.S. Pat. No. 4,508,703, producing about 21 g of a fine powder.

B - Preparation of a composition in the form of a suspension of liposomes which is advantageously homogenized 20 g of the powder obtained in step A are dispersed in an aqueous solution buffered to about pH 7.5 to give a final volume of 500 ml. In general, the solution used is a solution containing 0.8% of NaCl and 1.5% of $NaH_2PO_4$—called "phosphate buffer"—to which an antioxidizing stabilizer, such as ascorbic acid at a concentration of 0.05%, has been added.

This gives a suspension of liposomes after homogenization either by means of ultrasound or in a homogenizer under pressure, for example by the process described in U.S. Pat. No. 4,621,023.

If, for example, homogenization is effected by treatment with ultrasound for 10 minutes, a mean liposome size of the order of 112 nanometers is obtained.

It will be seen that various dilutions can be prepared by modifying the amount of extracts added at the start or by increasing the volume of the solution of dispersion, which represents an easy process for the preparation of various concentrations of extract.

If dilution is not carried out, 500 ml of homogenized suspension are obtained after this step B.

C - Preparation of a homogenized composition of liposomes in the form of a gel This homogenized suspension can be gelled by mixing with a gel, such as a vinylic polymer gel, in particular that marketed under the tradename Carbopol ® 940.

Thus, to prepare this gel in the conventional manner, 25 g of Carbopol ® 940 are dispersed in 500 g of water in the presence of a preservative and a customary chelating agent, and then, after swelling, the dispersion is neutralized to pH 7.5 with triethanolamine. 500 ml of the said gel are added to the 500 ml of homogenized suspension obtained in step B above to give a total volume of 1000 ml.

In this gelled composition, the concentration of dry extract of the bark of mulberry root is about 0.073% and the concentration of lecithin is 2%.

EXAMPLE 2

Composition of liposomes containing extract of the bark of mulberry root and kojic acid The procedure of Example 1-A is followed except that 10 g of kojic acid are added either direct to the extract or, preferably, to the methylene chloride.

This gives a powder containing kojic acid with the dry extract of mulberry.

This powder can be dispersed according to the procedure described in Example 1-B and the homogenized solution obtained can then be gelled according to the procedure of Example 1-C.

EXAMPLE 3

Composition of liposomes containing extract of the bark of mulberry root and hydroquinone The procedure of Example 1-A is followed except that 20 g of hydroquinone are added either direct to the extract or, preferably, to the methylene chloride.

Likewise, the powder obtained, containing hydroquinone with the dry extract of mulberry, can be dispersed according to the procedure described in Example 1-B and the homogenized solution obtained can then be gelled according to the procedure described in Example 1-C.

EXAMPLE 4

Composition of liposomes containing extract of the bark of mulberry root, kojic acid and hydroquinone The procedure of Example 1-A is followed except that 10 g of kojic acid and 20 g of hydroquinone are added either to the extract or, preferably, to the methylene chloride.

Moreover, in a preferred embodiment, 4 g of sodium sulfite and 5 g of L-ascorbic acid are added to the buffered aqueous solution as antioxidants in the case of the atomization process.

EXAMPLE 5

Gel of liposomes containing an extract of mulberry bark

Instead of being incorporated into the phospholipidic phase, the active principles of the mulberry are introduced into the aqueous phase in the following manner:

8 ml of an extract of the bark of mulberry shoots containing about 1% of dry residue are dissolved in 100 ml of phosphate buffer. 2 g of an intimate mixture of lecithin and sitosterol (9:1), obtained by atomization (according to U.S. Pat. No. 4,508,703), are added to this solution. The resulting solution is treated with ultrasound until the liposome size obtained is less than 150 nm. 100 g of an aqueous gel of Carbopol ® 940 are added.

EXAMPLE 6

Use of compositions according to Examples 1 to 3 for the preparation of a pharmaceutical or cosmetic composition The use of the composition of Example 1 as a pharmaceutical composition, especially a dermatological composition, or a cosmetic composition is examined by carrying out the following experiments in vivo.

Demonstration of the skin-lightening activity

As a first alternative, the skin-lightening activity of the compositions according to the invention is studied using hairless mice with pigmented tails, which are obtained in a proportion of 90% in the litter resulting from two successive crossbreedings, the first of which is carried out by crossbreeding a black female C57 mouse with a male BL6-HRO or eb-HRO mouse, available from the centre de sélection et d'élevage d'animaux de laboratoire (center for the selection and breeding of laboratory animals), abbreviated to CSEAL, of the CNRS in Orléans, and the males of the litter are then cross-bred again with a black female C57 mouse.

A second alternative is to use hairless mice with pigmented ears and black eyes, Skh:HR-2, available from the Temple University of Health Sciences, Central Animal Facility, in Philadelphia.

To perform the experiments, the product obtained in the form of a gel in Example 1 is applied to a pigmented zone for 5 days a week for 6 weeks, using a group of ten mice.

Fragments of skin from the tail or ears are then removed from each mouse, by biopsy, in the zones where the product has been applied and these fragments are placed in a solution of sodium bromide for 2 hours in order to separate the epidermis therefrom.

Samples of these epidermides are placed between two quartz slides. They are dried and then weighed.

These dried and weighed epidermis fragments are then subjected to digestion by trypsin at 37° C. for 48 hours.

This is followed by filtration and centrifugation at 3000 rpm for 30 minutes.

The melaniferous residue corresponding to each mouse is recovered and suspended in distilled water in an amount necessary for measurement of the optical density. Ten different samples are thus obtained.

The optical density of these 10 samples is measured in the conventional manner at 400 nm.

The values recorded for these 10 samples are then adjusted to correspond to a weight of 100 mg of epidermis removed and a mean optical density value is determined; this is the only value taken into account and is entered in Table I below.

Comparative tests were also carried out with a gel containing 0.073% by weight of dry extract of the bark of mulberry root, originating from the same lot as that used in Example 1 (composition $A_1$)

Another comparative composition containing only the reference gel (composition $A_2$) was prepared.

Of course, the gel used for the comparative compositions is identical to that used to prepare the composition of Example 1.

Another comparative composition (composition $A_3$) uses the "Kligman trio", which, as mentioned previously, includes vitamin A acid and an anti-inflammatory corticoid (dexamethasone).

The skin-lightening activity is also determined by comparison with the results obtained using the Kligman trio, according to the following formula:

$$\text{Skin-lightening activity} = \frac{OD_T - OD_A}{OD_T - OD_{K.T.}} \times 100$$

in which:

$OD_A$ = optical density obtained with the active composition tested (invention Ex. 1 or comparison $A_1$, $A_2$ or $A_3$)

$OD_T$ = optical density obtained with reference composition $A_2$ $OD_{K.T.}$ = optical density obtained with composition $A_3$ of the Kligman trio taken as a positive reference.

It can be seen from the Table of test results that the best skin-lightening efficacy is achieved by using vitamin A acid.

Furthermore, a gel containing 0.073% of dry extract of mulberry (composition $A_1$) does not improve the skin-lightening activity relative to the reference composition ($A_3$).

On the other hand, a synergistic effect can be observed on incorporating the extract of the bark of mulberry root into liposomes (a value of 356 compared with 509 for the reference and 530 for the gel of the same extract without liposomes).

The actual change is from a non-existent activity for composition $A_1$ compared with reference composition $A_3$ to an activity of about 37% for the composition of Example 1, according to the invention, compared with this same reference composition $A_3$.

Furthermore, the compositions according to the invention have no side effects and, in particular, do not have the irritant effect of vitamin A acid, which has always placed a significant restriction on the use of the "Kligman trio".

Thus the composition according to the invention proves very advantageous as a substitute for the Kligman trio, which has the major disadvantages mentioned above.

Various Examples of dermatological and dermatocosmetic compositions are given below.

EXAMPLE 7

Anti-blemish cosmetic composition for the face, according to the invention

This composition consists of the gel obtained in the crude state in Example 1-C, which is applied morning and evening to the melaniferous blemishes on the face until they have been lightened.

EXAMPLE 8

Anti-blemish hand cream

A cream is prepared simply by mixing the following components in the following proportions, which are indicated in grams:

| | |
|---|---|
| powder obtained in Example 1-A (having a ratio lecithin:dry extract of mulberry of 9.65:0.35) | 1 g |
| phosphate buffer | 29 g |
| stabilized W/O emulsion | 70 g |
| | 100 g |

EXAMPLE 9

Anti-blemish dermatocosmetic composition according to the invention

The components are used in the following proportions:

| | |
|---|---|
| powder obtained in Example 2 (containing lecithin and dry extract of mulberry in a ratio of 9.65:0.35, with kojic acid) | 3 g |
| phosphate buffer | 47 g |
| gel with preservative | 50 g |
| | 100 g |

To prepare the composition, the powder is first dispersed in the phosphate buffer and then the gel is added to give a composition in the form of a gel, with heating if necessary, according to the procedures described in Example 1-B and 1-C.

EXAMPLE 10

Anti-blemish liposomal dermatological composition according to the invention

The following components are used in the following proportions in grams:

| | |
|---|---|
| powder obtained in Example 3 (containing lecithin and dry extract of mulberry in a ratio of 9.65:0.35, with hydroquinone) | 4 g |
| phosphate buffer | 46 g |
| gel with preservative | 50 g |
| | 100 g |

This composition is obtained by following the procedure of Example 9.

In all these Examples 8 to 10, the powder, containing kojic acid or hydroquinone if appropriate, is dispersed in the phosphate buffer according to the procedure described in Example 1-B, after which the dispersion can be gelled with the gel according to the procedure described in Example 1-C.

TABLE I

| Results of skin-lightening activity tests | | | | |
|---|---|---|---|---|
| Composition | Ex. 1 | $A_1$ | $A_2$ | $A_3$ |
| Optical density per weight of 100 mg of epidermis removed | 356 | 530 | 509 | 94 |
| Efficacy compared with $A_3$ (expressed in %) | 37 | NS | 0 | 100 |

NS = not significant

What is claimed is:

1. A composition, comprising hydrated lipidic lamellar phases or liposomes containing an active ingredient selected from the group consisting of
   (a) a mulberry extract obtained by extraction with a polar solvent and
   (b) a flavone contained in said extract and either isolated from the extract or separately chemically synthesized;
   the active ingredient being incorporated in the composition in an amount effective to impart skin-lightening activity thereto.
2. The composition of claim 1, wherein the active ingredient additionally includes
   (c) kojic acid or a salt or ester thereof; or
   (d) hydroquinone; or
   (e) a mixture of (c) and (d);
   the active ingredient, in the aggregate, being incorporated in the composition in an amount effective to impart skin-lightening activity thereto.
3. The composition of claim 1, wherein the mulberry extract is selected from the group consisting of Morus Alba L. and Morus Rubra extract.
4. The composition of claim 1, wherein said flavone is a kuwanone.
5. The composition of claim 1, wherein said polar solvent comprises a solvent selected from the group consisting of an alcoholic solution and an aqueous alcoholic solution.
6. The composition of claim 1, wherein the mulberry extract is selected from the group consisting of a dry extract of leaves, ends of stems, bark of shoots, or bark of roots of mulberry.
7. The composition of claim 1, wherein the mulberry component is incorporated into the lipidic phase of the hydrated lipid lamellar phases or of the liposomes.
8. The composition of claim 1, wherein the mulberry component is incorporated into the aqueous phase of the hydrated lipid lamellar phases or of the liposomes.
9. The composition of claim 1, further comprising a gel wherein the gel comprises vinylic polymer gel present in a ratio to water of from 1 gram to 20 grams.
10. The composition of claim 9, further comprising phosphate buffer present in an amount ranging from 46 to 47% by weight of the composition, wherein the gel is present in an amount of 50% by weight of the composition.
11. The composition of claim 1, further comprising a cream containing by weight of the composition 29% phosphate buffer and 70% water/oil emulsion.
12. A composition, comprising hydrated lipidic lamellar phases or liposomes containing an active ingredient selected from the group consisting of
    (a) a mulberry extract obtained by extraction with a polar solvent and
    (b) a flavone contained in said extract and either isolated from the extract or separately chemically synthesized;
    the active ingredient being incorporated in an amount of from 0.005 to 1% by weight of the composition.
13. The composition of claim 12, wherein the active ingredient additionally includes:
    (c) kojic acid or a salt or ester thereof in an amount of from 0.5 to 4% by weight of the composition; or
    (d) hydroquinone in an amount of from 0.5 to 6% by weight of the composition; or
    (e) a mixture of (c) and (d).
14. The composition of claim 12, wherein said mulberry extract is selected from the group consisting of Morus Alba L. and Morus Rubra extract.
15. The composition of claim 12, wherein said flavone is a kuwanone.
16. The composition of claim 12, wherein said polar solvent comprises a solvent selected from the group consisting of an alcoholic solution and an aqueous alcoholic solution.
17. The composition of claim 12, wherein the mulberry extract is selected from the group consisting of a dry extract of leaves, ends of stems, bark of shoots, or bark of roots of mulberry.
18. The composition of claim 12, wherein the mulberry component is incorporated into the lipid phase of the hydrated lipid lamellar phases or of the liposomes.

19. The composition of claim 12, wherein the mulberry component is incorporated into the aqueous phase of the hydrated lipid lamellar phases or of the liposomes.

20. The composition of claim 12, further comprising a gel wherein the gel comprises vinylic polymer gel present in a ratio to water of from 1 gram to 20 grams.

21. The composition of claim 20, further comprising phosphate buffer present in an amount ranging from 46 to 47% by weight of the composition, wherein the gel is present in an amount of 50% by weight of the composition.

22. The composition of claim 12, further comprising a cream containing by weight of the composition 29% phosphate buffer and 70% water/oil emulsion.

23. A method for the cosmetic treatment of a subject whose skin is to be treated for anti-inflammatory or skin-lightening purposes, comprising applying to the skin a composition comprising hydrated lipidic lamellar phases or liposomes containing an active ingredient selected from the group consisting of
  (a) a mulberry extract obtained by extraction with a polar solvent and
  (b) a flavone contained in said extract and either isolated from the extract or separately chemically synthesized;
  the active ingredient being incorporated in the composition in an amount sufficient to effect said cosmetic treatment.

24. The method of claim 23, wherein the active ingredient additionally includes
  (c) kojic acid or a salt or ester thereof; or
  (d) hydroquinone; or
  (e) a mixture of (c) and (d);
  the active ingredient, in the aggregate, being incorporated in the composition in an amount sufficient to effect such cosmetic treatment.

25. The method of claim 23, wherein said mulberry extract is selected from a group consisting of Morus Alba L. and Morus Rubra extract.

26. The method of claim 23, wherein said flavone is a kuwanone.

27. The method of claim 23, wherein said polar solvent comprises a solvent selected from the group consisting of an alcoholic solution and an aqueous alcoholic solution.

28. The method of claim 23, wherein the mulberry extract is selected from the group consisting of a dry extract of leaves, ends of stems, bark of shoots, or bark of roots of mulberry.

29. The method of claim 23, wherein the mulberry component is incorporated into the lipidic phase of the hydrated lipid lamellar phases or of the liposomes.

30. The method of claim 23, wherein the mulberry component is incorporated into the aqueous phase of the hydrated lipid lamellar phases or of the liposomes.

31. The method of claim 23, wherein the composition further comprises a gel comprised of vinylic polymer gel present in a ratio to water of from 1 gram to 20 grams.

32. The method of claim 31, wherein the composition further comprises phosphate buffer present in an amount ranging from 46 to 47% by weight of the composition, wherein the gel is present in an amount of 50% by weight of the composition.

33. The method of claim 23, wherein the composition further comprises a cream containing by weight of the composition 29% phosphate buffer and 70% water/oil emulsion.

34. The method for the cosmetic treatment of a subject whose skin is to be treated for anti-inflammatory or skin lightening purposes, comprising applying to the skin a composition comprising hydrated lipidic lamellar phases or liposomes containing an active ingredient selected from the group consisting of
  (a) a mulberry extract obtained by extraction with a polar solvent and
  (b) a flavone contained in said extract and either isolated from the extract or separately chemically synthesized;
  the active ingredient being incorporated in an amount of from 0.005% to 1% by weight of the composition.

35. The method of claim 34, wherein the active ingredient additionally includes
  (c) kojic acid or a salt or ester thereof; or
  (d) hydroquinone; or
  (e) a mixture of (c) and (d);
  the active ingredient, in the aggregate, being incorporated in the composition in an amount sufficient to effect such cosmetic treatment.

36. The method of claim 34, wherein said mulberry extract is selected from the group consisting of Morus Alba L. and Morus Rubra extract.

37. The method of claim 34, wherein said flavone is a kuwanone.

38. The method of claim 34, wherein said polar solvent comprises a solvent selected from the group consisting of an alcoholic solution and an aqueous alcoholic solution.

39. The method of claim 34, wherein the mulberry extract is selected from the group consisting of a dry extract of leaves, ends of stems, bark of shoots, or bark of roots of mulberry.

40. The method of claim 34, wherein the mulberry component is incorporated into the lipidic phase of the hydrated lipid lamellar phases or of the liposomes.

41. The method of claim 34, wherein the mulberry component is incorporated into the aqueous phase of the hydrated lipid lamellar phases or of the liposomes.

42. The method of claim 34, wherein the composition comprises a gel comprised of vinylic polymer gel present in a ratio to water of from 1 gram to 20 grams.

43. The method of claim 42, wherein the composition further comprises phosphate buffer present in an amount ranging from 46 to 47% by weight of the composition, wherein the gel is present in an amount of 50% by weight of the composition.

44. The method of claim 34, wherein the composition further comprises a cream containing by weight of the composition 29% phosphate buffer and 70% water/oil emulsion.

45. A method for the pharmaceutical treatment of a patient whose skin is to be treated for anti-inflammatory or skin-lightening purposes, comprising applying to the skin a composition comprising hydrated lipidic lamellar phases or liposomes containing an active ingredient selected from the group consisting of
  (a) a mulberry extract obtained by extraction with a polar solvent and
  (b) a flavone contained in said extract and either isolated from the extract or separately chemically synthesized;

the active ingredient being incorporated in the composition in an amount sufficient to effect said pharmaceutical treatment.

46. The method of claim 45, wherein the active ingredient additionally includes
   (c) kojic acid or a salt or ester thereof; or
   (d) hydroquinone; or
   (e) a mixture of (c) and (d),
the active ingredient, in the aggregate, being incorporated in the composition in an amount sufficient to effect said pharmaceutical treatment.

47. The method of claim 45, wherein said mulberry extract is selected from the group consisting of Morus Alba L. and Morus Rubra extract.

48. The method of claim 45, wherein said flavone is a kuwanone.

49. The method of claim 45, wherein said polar solvent comprises a solvent selected from the group consisting of an alcoholic solution and an aqueous alcoholic solution.

50. The method of claim 45, wherein the mulberry extract is selected from the group consisting of a dry extract of leaves, ends of stems, bark of shoots, or bark of roots of mulberry.

51. The method of claim 45, wherein the mulberry component is incorporated into the lipidic phase of the hydrated lipid lamellar phases or of the liposomes.

52. The method of claim 45, wherein the mulberry component is incorporated into the aqueous phase of the hydrated lipid lamellar phases or of the liposomes.

53. The method of claim 45, wherein the composition further comprises a gel comprised of vinylic polymer gel present in a ratio to water from 1 gram to 20 grams.

54. The method of claim 54, wherein the composition further comprises phosphate buffer present in an amount ranging from 46 to 47% by weight of the composition, wherein the gel is present in an amount of 50% by weight of the composition.

55. The method of claim 45, wherein the composition further comprises a cream containing by weight of the composition 29% phosphate buffer and 70% water/oil emulsion.

56. A method for the pharmaceutical treatment of a patient whose skin is to be treated for anti-inflammatory or skin-lightening purposes, comprising applying to the skin a composition comprising hydrated lipidic lamellar phases or liposomes containing an active ingredient selected from the group consisting of
   (a) a mulberry extract obtained by extraction with a polar solvent, and
   (b) a flavone contained in said extract and either isolated from the extract or separately chemically synthesized;
the active ingredient being incorporated in an amount of from 0.005 to 1% by weight of the composition.

57. The method of claim 56, wherein said mulberry extract is selected from the group consisting of Morus Alba L. and Morus Rubra extract.

58. The method of claim 56, wherein said flavone is a kuwanone.

59. The method of claim 56, wherein said polar solvent comprises a solvent selected from the group consisting of an alcoholic solution and an aqueous alcoholic solution.

60. The method of claim 56, wherein the active ingredient additionally includes
   (c) kojic acid or a salt or ester thereof in an amount of from 0.5 to 4% by weight of the composition; or
   (d) hydroquinone in an amount of from 0.5% to 6% by weight of the composition; or
   (e) a mixture of (c) and (d).

61. The method of claim 56, wherein the mulberry extract is selected from the group consisting of a dry extract of leaves, ends of stems, bark of shoots, or bark of roots of mulberry.

62. The method of claim 56, wherein the mulberry component is incorporated into the lipidic phase of the hydrated lipid lamellar phases or of the liposomes.

63. The method of claim 56, wherein the mulberry component is incorporated into the aqueous phase of the hydrated lipid lamellar phases or of the liposomes.

64. The method of claim 56, wherein the composition further comprises a gel comprised of vinylic polymer gel present in a ratio to water of from 1 gram to 20 grams.

65. The method of claim 64, wherein the composition further comprises phosphate buffer present in an amount ranging from 46 to 47% by weight of the composition, wherein the gel is present in an amount of 50% by weight of the composition.

66. The method of claim 56, wherein the composition further comprises a cream containing by weight of the composition 29% phosphate buffer and 70% water/oil emulsion.

* * * * *

UNITED STATES PATENT AND TRADEMARK OFFICE
CERTIFICATE OF CORRECTION

PATENT NO. : 5,164,182

DATED : November 17, 1992

INVENTOR(S): ALAIN MEYBECK, FREDERIC BONTE

It is certified that error appears in the above-identified patent and that said Letters Patent is hereby corrected as shown below:

Column 10, line 67: In claim 18, before "phase" delete "lipid" and insert --lipidic--.

Column 12, line 3: In claim 34, before "method" delete "The" and insert -- A --.

Column 13, line 35: In claim 53, before "from" insert --of--.

Column 13, line 36: In claim 54, after "claim" delete "54" and insert --53--.

Column 14, line 25: In claim 60, before "a mixture" delete "(a)" and insert --(e)--.

Signed and Sealed this

Thirtieth Day of November, 1993

Attest:

BRUCE LEHMAN

Attesting Officer

Commissioner of Patents and Trademarks